United States Patent
Karlsson (10) Patent No.: US 10,151,694 B2
(45) Date of Patent: Dec. 11, 2018

(54) METHOD AND SYSTEM FOR SENSOR RESPONSE CURVE EVALUATION

(75) Inventor: Olof Karlsson, Uppsala (SE)

(73) Assignee: GE HEALTHCARE BIO-SCIENCES AB, Uppsala (SE)

(*) Notice: Subject to any disclaimer, the term of this patent is extended or adjusted under 35 U.S.C. 154(b) by 0 days.

(21) Appl. No.: 13/512,420

(22) PCT Filed: Nov. 29, 2010

(86) PCT No.: PCT/SE2010/051311
§ 371 (c)(1),
(2), (4) Date: May 29, 2012

(87) PCT Pub. No.: WO2011/065913
PCT Pub. Date: Jun. 3, 2011

(65) Prior Publication Data
US 2012/0244638 A1   Sep. 27, 2012

(30) Foreign Application Priority Data
Nov. 30, 2009  (SE) ...................................... 0950914

(51) Int. Cl.
G01N 33/557 (2006.01)
G01N 33/543 (2006.01)
(Continued)

(52) U.S. Cl.
CPC ........... *G01N 21/553* (2013.01); *G01N 21/27* (2013.01); *G01N 21/272* (2013.01);
(Continued)

(58) Field of Classification Search
None
See application file for complete search history.

(56) References Cited

U.S. PATENT DOCUMENTS 6,586,193 B2 *  7/2003  Yguerabide et al. ............. 506/3
7,060,448 B2 *  6/2006  Henderson et al. .......... 435/7.1
(Continued)

FOREIGN PATENT DOCUMENTS

| WO | 01/69245 | 9/2001 |
| WO | WO 2005/114218 | 12/2005 |
| WO | WO 2009/14985 | 1/2009 |

OTHER PUBLICATIONS

Nordin, H. et al. "Kinetic studies of small molecule interactions with protein kinases using biosensor technology", Analytical Biochemistry, (2005) 340(2):359-364.*

(Continued)

*Primary Examiner* — Scott Long
*Assistant Examiner* — Gary E Hollinden
(74) *Attorney, Agent, or Firm* — Hanley, Flight and Zimmerman, LLC (57) ABSTRACT

A method of evaluating an interaction parameter for the interaction between a plurality of analytes and a ligand using a biosensor, which comprises the steps of:
A: providing a sensor surface having the ligand immobilized thereto,
B: contacting the sensor surface with the plurality of analytes,
C: registering a sensor response curve for each one of the plurality of analytes,
D: extracting interaction parameters from each sensor response curve,
E: evaluating each sensor response curve according to one or more binding behavior criteria,
F: displaying the interaction parameters in a diagram, wherein interaction parameters relating to response curves meeting a binding behavior criteria are graphically (Continued)

distinguishable from interaction parameters relating to response curves meeting another or no binding behavior criteria.

7 Claims, 7 Drawing Sheets (51) Int. Cl.
G01N 21/27 (2006.01)
G01N 21/552 (2014.01)
G01N 21/77 (2006.01)

(52) U.S. Cl.
CPC ....... *G01N 21/552* (2013.01); *G01N 21/7703* (2013.01); *G01N 33/54373* (2013.01); *G01N 33/557* (2013.01)

(56) References Cited

U.S. PATENT DOCUMENTS

| 9,063,156 B2 * | 6/2015 | Korlach | C12Q 1/6825 |
| 2002/0019019 A1 * | 2/2002 | Hamalainen et al. | 435/7.92 |
| 2002/0182717 A1 * | 12/2002 | Karlsson | 435/287.2 |
| 2003/0096432 A1 | 5/2003 | Jakobsen | |
| 2005/0131650 A1 | 6/2005 | Andersson et al. | |
| 2005/0255527 A1 * | 11/2005 | Yang et al. | 435/7.1 |
| 2007/0016378 A1 | 1/2007 | Andersson | |
| 2008/0299673 A1 | 12/2008 | Wagner et al. | |
| 2011/0065597 A1 * | 3/2011 | Williams et al. | 506/9 |
| 2013/0065251 A1 * | 3/2013 | Karlsson et al. | 435/7.8 |
| 2014/0323328 A1 * | 10/2014 | Dale et al. | 506/9 |
| 2015/0346104 A1 * | 12/2015 | Chou | G01N 21/763 436/501 |

OTHER PUBLICATIONS

Stenlund, P. et al. "Studies of small molecule interactions with protein phosphatases using biosensor technology", Analytical Biochemistry, (2006) 353:217-225.*
Buhl, A., et al., Biosensors and Bioelectronics, 25 (2009) 198-203.
Katsamba, P., et al., Methods, 26 (2002) 95-104.
European Office Action for EP Application No. 10833675.1 dated Nov. 9, 2015 (8 pages).
Karlsson et al., "Analyzing a Kinetic Titration Series Using Affinity Biosensors," Analytical Biochemistry, 2006, 349:136-147.
Nieba et al., "BIACORE Analysis of Histidine-Tagged Proteins Using a Chelating NTA Sensor Chip," Analytical Biochemistry, 1997, 252:217-228.
European Office Action for EP Application No. 10833675.1 dated Oct. 10, 2016 (11 pages).
Khalifa et al., "BIACORE Data Processing: An Evaluation of the Global Fitting Procedure," Analytical Biochemistry, 2001, 293:194-203.

* cited by examiner

PRIOR ART

Fig. 1

PRIOR ART

METHOD AND SYSTEM FOR SENSOR RESPONSE CURVE EVALUATION

CROSS-REFERENCE TO RELATED APPLICATIONS

This application is a filing under 35 U.S.C. 371 of international application number PCT/SE2010/051311, filed Nov. 29, 2010, published on Jun. 3, 2011 as WO 2011/065913, which claims priority to application number 0950914-2 filed in Sweden on Nov. 30, 2009.

FIELD OF THE INVENTION

The present invention relates to a method of analysing molecular binding interactions at a sensing surface, and more particularly to a method of binding behaviour analysis for the interaction between an analyte and a ligand using a biosensor

BACKGROUND OF THE INVENTION

Analytical sensor systems that can monitor interactions between molecules, such as biomolecules, in real time are gaining increasing interest. These systems are often based on optical biosensors and usually referred to as interaction analysis sensors or biospecific interaction analysis sensors. A representative such biosensor system is the BIACORE® instrumentation sold by Biacore AB (Uppsala, Sweden) which uses surface plasmon resonance (SPR) for detecting interactions between molecules in a sample and molecular structures immobilized on a sensing surface. As sample is passed over the sensor surface, the progress of binding directly reflects the rate at which the interaction occurs. Injection of sample is followed by a buffer flow during which the detector response reflects the rate of dissociation of the complex on the surface. A typical output from the BIACORE® system is a graph or curve describing the progress of the molecular interaction with time, including an association phase part and a dissociation phase part. This binding curve, which is usually displayed on a computer screen, is often referred to as a "sensorgram".

With the BIACORE® system (and analogous sensor systems) it is thus possible to determine in real time without the use of labeling, and often without purification of the substances involved, not only the presence and concentration of a particular molecule (analyte) in a sample, but also additional interaction parameters, including kinetic rate constants for binding (association) and dissociation in the molecular interaction as well as the affinity for the surface interaction. The association rate constant ($k_a$) and the dissociation rate constant ($k_d$) can be obtained by fitting the resulting kinetic data for a number of different sample analyte concentrations to mathematical descriptions of interaction models in the form of differential equations. The affinity (expressed as the affinity constant $K_A$ or the dissociation constant $K_D$) can be calculated from the association and dissociation rate constants. Many times, however, it may be difficult to obtain definitive kinetic data, and it is therefore usually more reliable to measure the affinity by equilibrium binding analysis, which involves determining, for a series of analyte concentrations, the level of binding at equilibrium, or steady state, which is presumed to have been reached at or near the end of the association phase of the binding interaction. To ensure that the association phase of the binding curve is indeed likely to have reached steady state, one usually determines in advance the necessary time length of sample injection (i.e. sample contact time with the sensor chip surface) for the bound analyte to reach equilibrium under the conditions intended to be used for the affinity measurements. Since both the time taken to reach equilibrium and the time it takes for the analyte to dissociate are governed primarily by the dissociation rate constant, approximate injection times may also be estimated from the dissociation constant.

SUMMARY OF THE INVENTION

The object of the invention is to provide a new method and biosensor system for binding behavior analysis for the interaction between an analyte and a ligand using a biosensor, which method and biosensor system overcomes one or more drawbacks of the prior art. This is achieved by the method and biosensor system as defined in the independent claims.

Binding behaviour markers are expected to be very useful tools when frequently evaluating large data sets improving the evaluation throughput significantly and thereby the overall screening throughput.

A more complete understanding of the present invention, as well as further features and advantages thereof, will be obtained by reference to the following detailed description and drawings.

DETAILED DESCRIPTION OF THE INVENTION

Unless defined otherwise, all technical and scientific terms used herein have the same meaning as commonly understood by a person skilled in the art related to this invention. Also, the singular forms "a", "an", and "the" are meant to include plural reference unless it is stated otherwise.

All publications, patent applications, patents, and other references mentioned herein are incorporated by reference in their entirety.

As mentioned above, the present invention relates to the evaluation of steady state binding data for a molecular binding interaction from a plurality of data sets for the interaction to determine one or more interaction parameters for the interaction, wherein other interaction data from a data set than steady state binding data is used to estimate the reliability of the steady state binding data of the data set. Typically, the experimental binding data is obtained by sensor based technology which studies the molecular interactions and present the results in real time as the interactions progress. Before describing the present invention in more detail, however, the general context in which the invention is intended to be used will be described.

Chemical sensors or biosensors are typically based on label-free techniques, detecting a change in a property of a sensor surface, such as e.g. mass, refractive index, or thickness for the immobilised layer, but there are also sensors relying on some kind of labelling. Typical sensor detection techniques include, but are not limited to, mass detection methods, such as optical, thermo-optical and piezoelectric or acoustic wave methods (including e.g. surface acoustic wave (SAW) and quartz crystal microbalance (QCM) methods), and electrochemical methods, such as potentiometric, conductometric, amperometric and capacitance/impedance methods. With regard to optical detection methods, representative methods include those that detect mass surface concentration, such as reflection-optical methods, including both external and internal reflection methods, which are angle, wavelength, polarization, or phase resolved, for example evanescent wave ellipsometry and evanescent wave spectroscopy (EWS, or Internal Reflection Spectroscopy), both of which may include evanescent field enhancement via surface plasmon resonance (SPR), Brewster angle refractometry, critical angle refractometry, frustrated total reflection (FTR), scattered total internal reflection (STIR) (which may include scatter enhancing labels), optical wave guide sensors; external reflection imaging, evanescent wave-based imaging such as critical angle resolved imaging, Brewster angle resolved imaging, SPR-angle resolved imaging, and the like. Further, photometric and imaging/microscopy methods, "per se" or combined with reflection methods, based on for example surface enhanced Raman spectroscopy (SERS), surface enhanced resonance Raman spectroscopy (SERRS), evanescent wave fluorescence (TIRF) and phosphorescence may be mentioned, as well as waveguide interferometers, waveguide leaky mode spectroscopy, reflective interference spectroscopy (RIfS), transmission interferometry, holographic spectroscopy, and atomic force microscopy (AFR).

Commercially available biosensors include the aforementioned BIACORE® system instruments, manufactured and marketed by Biacore AB, Uppsala, Sweden, which are based on surface plasmon resonance (SPR) and permit monitoring of surface binding interactions in real time between a bound ligand and an analyte of interest. In this context, "ligand" is a molecule that has a known or unknown affinity for a given analyte and includes any capturing or catching agent immobilized on the surface, whereas "analyte" includes any specific binding partner thereto.

While in the detailed description and Examples that follow, the present invention is illustrated in the context of SPR spectroscopy, and more particularly the BIACORE® system, it is to be understood that the present invention is not limited to this detection method. Rather, any affinity-based detection method where an analyte binds to a ligand immobilised on a sensing surface may be employed, provided that a change at the sensing surface can be measured which is quantitatively indicative of binding of the analyte to the immobilised ligand thereon.

The phenomenon of SPR is well known, suffice it to say that SPR arises when light is reflected under certain conditions at the interface between two media of different refractive indices, and the interface is coated by a metal film, typically silver or gold. In the BIACORE® instruments, the media are the sample and the glass of a sensor chip which is contacted with the sample by a microfluidic flow system. The metal film is a thin layer of gold on the chip surface. SPR causes a reduction in the intensity of the reflected light at a specific angle of reflection. This angle of minimum reflected light intensity varies with the refractive index close to the surface on the side opposite from the reflected light, in the BIACORE® system the sample side.

Figure 1:
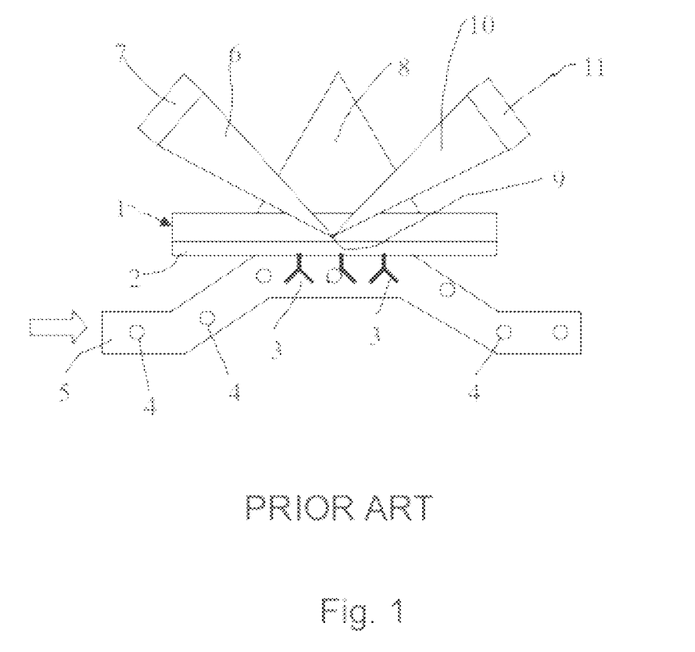
FIG. 1 is a schematic side view of a biosensor system based on SPR.

A schematic illustration of the BIACORE® system is shown in FIG. 1. Sensor chip 1 has a gold film 2 supporting capturing molecules (ligands) 3, e.g. antibodies, exposed to a sample flow with analytes 4, e.g. an antigen, through a flow channel 5. Monochromatic p-polarised light 6 from a light source 7 (LED) is coupled by a prism 8 to the glass/metal interface 9 where the light is totally reflected. The intensity of the reflected light beam 10 is detected by an optical detection unit 11 (photodetector array).

A detailed discussion of the technical aspects of the BIACORE® instruments and the phenomenon of SPR may be found in U.S. Pat. No. 5,313,264. More detailed information on matrix coatings for biosensor sensing surfaces is given in, for example, U.S. Pat. Nos. 5,242,828 and 5,436,161. In addition, a detailed discussion of the technical aspects of the biosensor chips used in connection with the BIACORE® instruments may be found in U.S. Pat. No. 5,492,840. The teachings of each of the patents mentioned above are incorporated by reference in their entirety. Included are any continuation and divisional applications relative to each of the above patents.

Figure 2:
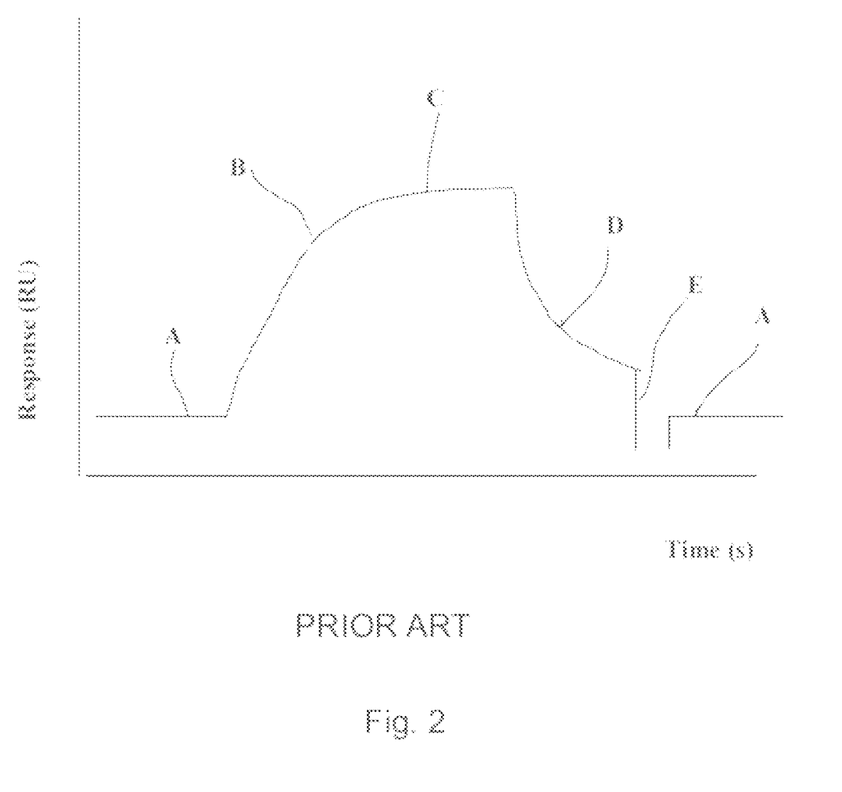
FIG. 2 is a representative sensorgram where the binding curve has visible association and dissociation phases.

When molecules in the sample bind to the capturing molecules on the sensor chip surface, the concentration, and therefore the refractive index at the surface changes and an SPR response is detected. Plotting the response against time during the course of an interaction will provide a quantitative measure of the progress of the interaction. Such a plot, or kinetic or binding curve (binding isotherm), is usually called a sensorgram, also sometimes referred to in the art as "affinity trace" or "affinogram". In the BIACORE® system, the SPR response values are expressed in resonance units (RU). One RU represents a change of 0.0001° in the angle of minimum reflected light intensity, which for most proteins and other biomolecules correspond to a change in concentration of about 1 pg/mm$^2$ on the sensor surface. As sample containing an analyte contacts the sensor surface, the capturing molecule (ligand) bound to the sensor surface interacts with the analyte in a step referred to as "association." This step is indicated on the sensorgram by an increase in RU as the sample is initially brought into contact with the sensor surface. Conversely, "dissociation" normally occurs when the sample flow is replaced by, for example, a buffer flow. This step is indicated on the sensorgram by a drop in RU over time as analyte dissociates from the surface-bound ligand.

A representative sensorgram (binding curve) for a reversible interaction at the sensor chip surface is presented in FIG. 2, the sensing surface having an immobilised capturing molecule, or ligand, for example an antibody, interacting with a binding partner therefor, or analyte, in a sample. The binding curves produced by biosensor systems based on other detection principles mentioned above will have a similar appearance. The vertical axis (y-axis) indicates the response (here in resonance units, RU) and the horizontal axis (x-axis) indicates the time (here in seconds). Initially, buffer is passed over the sensing surface giving the baseline response A in the sensorgram. During sample injection, an increase in signal is observed due to binding of the analyte. This part B of the binding curve is usually referred to as the "association phase". Eventually, a steady state condition is reached at or near the end of the association phase where the resonance signal plateaus at C (this state may, however, not always be achieved). It is to be noted that herein the term "steady state" is used synonymously with the term "equilibrium" (in other contexts the term "equilibrium" may be reserved to describe the ideal interaction model, since in practice binding could be constant over time even if a system is not in equilibrium). At the end of sample injection, the sample is replaced with a continuous flow of buffer and a decrease in signal reflects the dissociation, or release, of analyte from the surface. This part D of the binding curve is usually referred to as the "dissociation phase". The analysis is ended by a regeneration step where a solution capable of removing bound analyte from the surface, while (ideally) maintaining the activity of the ligand, is injected over the sensor surface. This is indicated in part E of the sensorgram. Injection of buffer restores the baseline A and the surface is now ready for a new analysis.

From the profiles of the association and dissociation phases B and D, respectively, information regarding the binding and dissociation kinetics is obtained, and the height of the resonance signal at C represents affinity (the response resulting from an interaction being related to the change in mass concentration on the surface). This will now be explained in more detail below.

Surface Binding Rate

Assume a reversible reaction between an analyte A and a surface-bound (immobilised) capturing molecule, or ligand, B which is not diffusion or mass transfer limited and obeys pseudo first order kinetics:

$$A+B \Leftrightarrow AB$$

This interaction model (usually referred to as the Langmuir model), which assumes that the analyte (A) is both monovalent and homogenous, that the ligand (B) is homogenous, and that all binding events are independent, is in fact applicable in the vast majority of cases.

The rate of change in surface concentration of analyte A (=rate of change in concentration of formed complex AB) during analyte injection is the sum of the rates of the analyte A going on and off:

$$\frac{d[AB]}{dt} = k_a[A][B] - k_d[AB] \quad (1)$$

where [A] is the concentration of analyte A, [B] is the concentration of the ligand B, [AB] is the concentration of the reaction complex AB, $k_a$ is the association rate constant, and $k_d$ is the dissociation rate constant.

After a time t, the concentration of unbound ligand B at the surface is $[B_T]-[AB]$, where $[B_T]$ is the total, or maximum, concentration of ligand B. Insertion into Equation (1) gives:

$$\frac{d[AB]}{dt} = k_a[A]\{[B_T] - [AB]\} - k_d[AB] \quad (2)$$

In terms of detector response units (AB is detected), this can be expressed as $$\frac{dR}{dt} = k_a C(R_{max} - R) - k_d R \quad (3)$$

where R is the response at time t in resonance units (RU), C is the initial, or bulk, concentration of free analyte (A) in solution, and $R_{max}$ is the response (in RU) obtained if analyte (A) had bound to all ligand (B) on the surface, also referred to as the saturation response. Rearrangement of Equation (3) gives:

$$\frac{dR}{dt} = k_a C R_{max} - (k_a C + k_d) R \quad (4)$$

where R is the response in resonance units (RU). In integrated form, the equation is:

$$R = \frac{k_a C R_{max}}{k_a C + k_d}(1 - e^{-(k_a C + k_d)t}) \quad (5)$$

Calculation of $k_a$ and $k_d$

Now, according to equation (4), if dR/dt is plotted against the bound analyte concentration R, the slope is $-(k_a C + k_d)$ and the vertical intercept is $k_a C R_{max}$. If the bulk concentration C is known and the saturation response $R_{max}$ has been determined (e.g. by saturating the surface with a large excess of analyte), the association rate constant $k_a$ and the dissociation rate constant $k_d$ can be calculated. A more convenient method is, however, fitting of the integrated function (5), or numerical calculation and fitting of the differential Equation (4), preferably by means of a computer program.

$k_d$ may also be determined in the following way. The rate of dissociation can be expressed as:

$$\frac{dR}{dt} = -k_d R \quad (6)$$

and in integrated form:

$$R = R_0 \cdot e^{-k_d t} \quad (7)$$

where $R_0$ is the response at the beginning of the dissociation phase (when the buffer wash of the surface starts).

Equation (6) may be linearized:

$$\ln\left[\frac{R}{R_0}\right] = -k_d t \quad (8)$$

and a plot of ln [$R/R_0$] versus t will produce a straight line with the slope=$-k_d$. More conveniently, however, the dissociation rate constant $k_d$ is determined by fitting the exponential rate equation (7).

To obtain reliable kinetic constants, the above described analysis is usually repeated for a number of different analyte concentrations and, suitably, also at at least one other ligand density at the sensor surface.

Calculation of Affinity

Affinity is expressed by the association constant $K_A = k_a/k_d$, or the dissociation constant (also referred to as the equilibrium constant) $K_D = k_d/k_a$.

The association constant $K_A$ may alternatively be determined from Equation (3), where dR/dt=0 at equilibrium, giving:

$$k_d R_{eq} = k_a C(R_{max} - R_{eq}) \quad (9)$$

where $R_{eq}$ is the detector response at equilibrium. Since $k_a/k_d=K_A$, insertion in Equation (9) and rearrangement gives:

$$\frac{R_{eq}}{C} = -K_A R_{eq} + K_A R_{max} \quad (10)$$

If binding reactions are performed at multiple concentrations, $K_A$ may be obtained by non-linear curve-fitting of the data. Alternatively, e.g. when the kinetic data is unreliable or association and dissociation are too rapid to measure accurately, $R_{eq}/C$ may be plotted versus $R_{eq}$, which gives the slope=$-K_A$ (Scatchard plot).

Rearrangement of Equation (10) gives:

$$R_{eq} = \frac{K_A C R_{max}}{1 + K_A C} \quad (11)$$

Insertion of $K_A=1/K_D$ into Equation (11) gives:

$$R_{eq} = \frac{C R_{max}}{K_D + C} \quad (12)$$

Usually, Equation (12) is modified to:

$$R_{eq} = \frac{C R_{max}}{K_D + C} + \text{Offset} \quad (13)$$

where "Offset" is a compensation factor for parallel baseline displacement due to systemic refractive index errors.

Equations (11) and (12) may be modified by introducing a steric interference factor n specifying how many binding sites are on average blocked by one analyte molecule:

$$R_{eq} = \frac{K_A C R_{max}}{1 + K_A C n} \quad (14)$$

$$R_{eq} = \frac{C R_{max}}{K_D + C n} \quad (15)$$

Software-Assisted Analysis

Software for the analysis of kinetic and affinity data is commercially available. Thus, for example, evaluation of kinetic and affinity data produced by the BIACORE® instruments is usually performed with the dedicated BIAevaluation software (supplied by Biacore AB, Uppsala, Sweden) using numerical integration to calculate the differential rate equations and non-linear regression to fit the kinetic and affinity parameters by finding values for the variables that give the closest fit, reducing the sum of squared residuals to a minimum.

Determining affinity constants from measured steady state binding levels with the BIAevaluation software involves the following steps:

(i) obtain steady state binding levels ($R_{eq}$) from report points on the sensorgrams in the steady state region of the curve;

(ii) create a plot of $R_{eq}$ against C; and (iii) fit this plot to a general "Steady state affinity" fitting model (e.g. Equation (13 or 14) to obtain $K_A/K_D$ and $R_{max}$.

The Invention

For interaction screening assays using biosensors, such as BIACORE® instruments, the interaction parameter used for evaluation is often the read out response of a defined point in the sensorgram (report point). The sensorgram, however, contains a lot more information about the interaction and the quality of the data, which justify an assessment of all the sensorgrams included. For large data sets (hundreds or thousands of sensorgrams) this can be a very tedious procedure.

In order to assess this limitation in evaluation of screening assays using biosensors, there is provided a computer implemented method of evaluating such screening assays. According to one embodiment, predefined criteria are provided for the shape of the sensorgrams that are relevant for the data evaluation along with criteria for response levels in relation to the stoichiometrically expected response and having these automatically pointed out by the software and brought to the result report.

Figure 3:
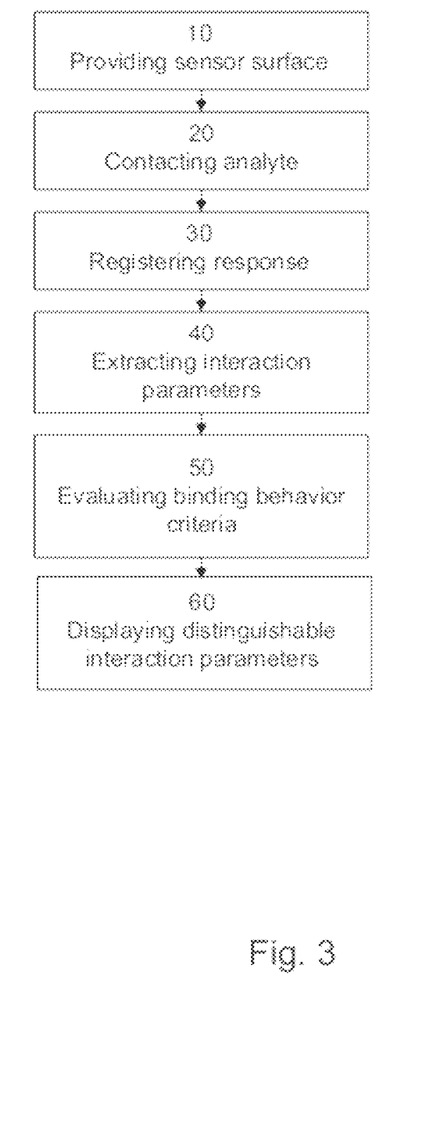
FIG. 3 is a schematic block diagram of a method according to the present invention.

According to one embodiment there is provided a method of evaluating an interaction parameter for the interaction between a plurality of analytes and a ligand using a biosensor, which comprises the steps of:

A: providing a sensor surface having the ligand immobilized thereto, FIG. 3 ref. 10, B: contacting the sensor surface with the plurality of analytes, FIG. 3 ref. 20, C: registering a sensor response curve for each one of the plurality of analytes, FIG. 3 ref. 30, D: extracting interaction parameters from each sensor response curve, FIG. 3 ref. 40, E: evaluating each sensor response curve according to two or more binding behavior criteria, FIG. 3 ref. 50, F: displaying the interaction parameters in a diagram, wherein interaction parameters relating to response curves meeting a binding behavior criteria are graphically distinguishable from interaction parameters relating to response curves meeting another or no binding criteria, FIG. 3 ref. 60.

Figure 4:
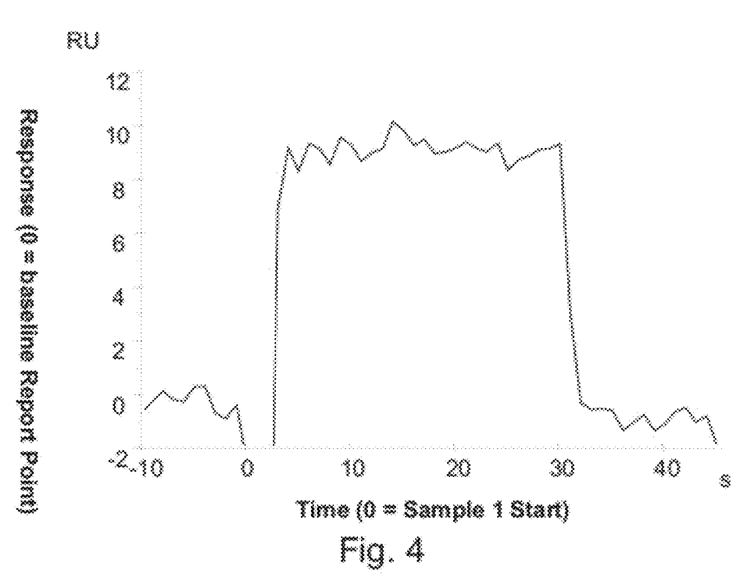
FIG. 4 shows a typical binding behavior of a drug molecule fragment.

The binding behavior criteria may be selected in many ways, depending on the particular assay to be performed, but in the disclosed embodiment, the binding behavior criteria are used to identify analytes that exhibit abnormal binding behavior whereas analytes that do not meet anyone of the disclosed criteria is considered to exhibit a "normal" binding behavior. FIG. 4 shows a typical binding behavior of a drug molecule fragment which is characterized by a fast on-rate and a fast off-rate with dissociation down to the baseline immediately after the sample injection. The typical behavior can be resembled as a square wave.

When analyzing screening assay data, the assay response is typically plotted along a sample number axis and one or several lines at defined response levels are used to divide the samples into two or more categories. It should be noted that other ways of graphically represent data may also be used in combination with the present binding behavior criteria.

Figure 5:
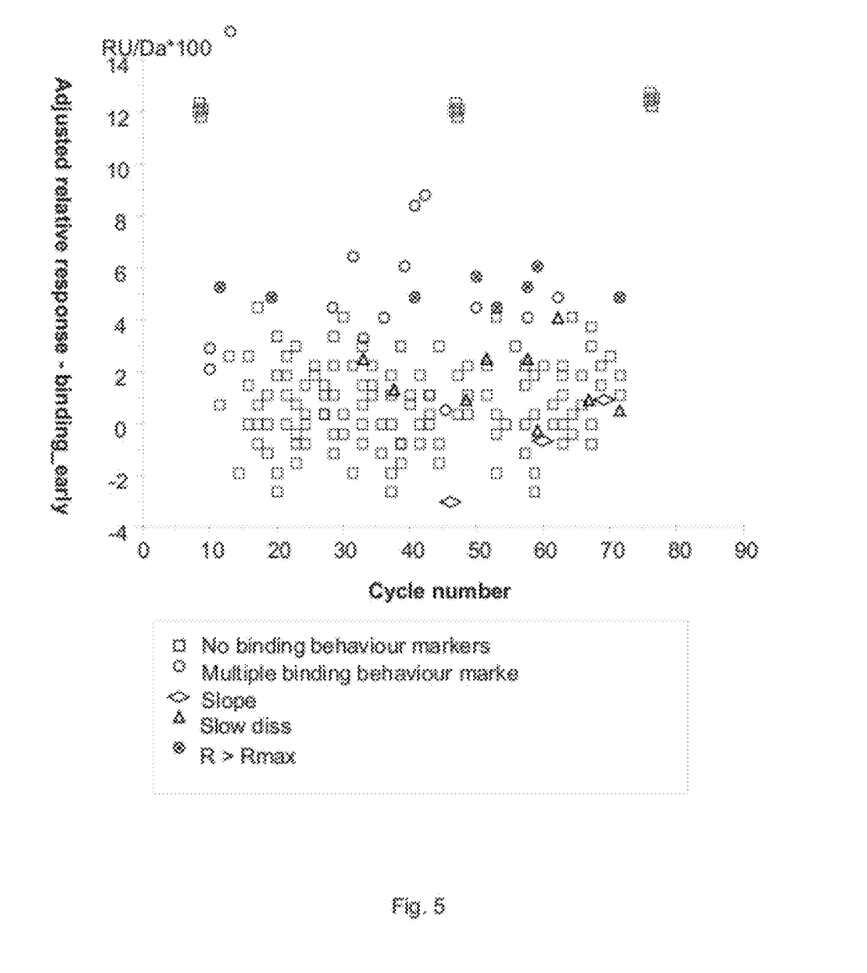
FIG. 5 shows a diagram, wherein interaction parameters relating to response curves meeting a binding behavior criteria are graphically distinguishable from interaction parameters relating to response curves meeting another or no binding behavior criteria according to the present invention.

FIG. 5 shows a diagram, wherein interaction parameters relating to response curves meeting a binding behavior criteria are graphically distinguishable from interaction parameters relating to response curves meeting another or no binding behavior criteria according to the present invention. In the disclosed embodiment, different binding behavior are distinguished by means of different shapes, but in alternative embodiments binding behavior may e.g. be distinguished by means of different colors or a combination thereof.

According to one embodiment, each point in the diagram is linked to the associated response curve, so that a user simply can mark the point to access the response curve. Moreover, the user is allowed to select deselect whole groups of analytes for further processing based on the binding behavior criteria that are met.

According to one embodiment, interaction parameters relating to response curves meeting two or more binding behavior criteria are graphically distinguishable from interaction parameters relating to response curves meeting no or one binding criteria.

Figure 6:
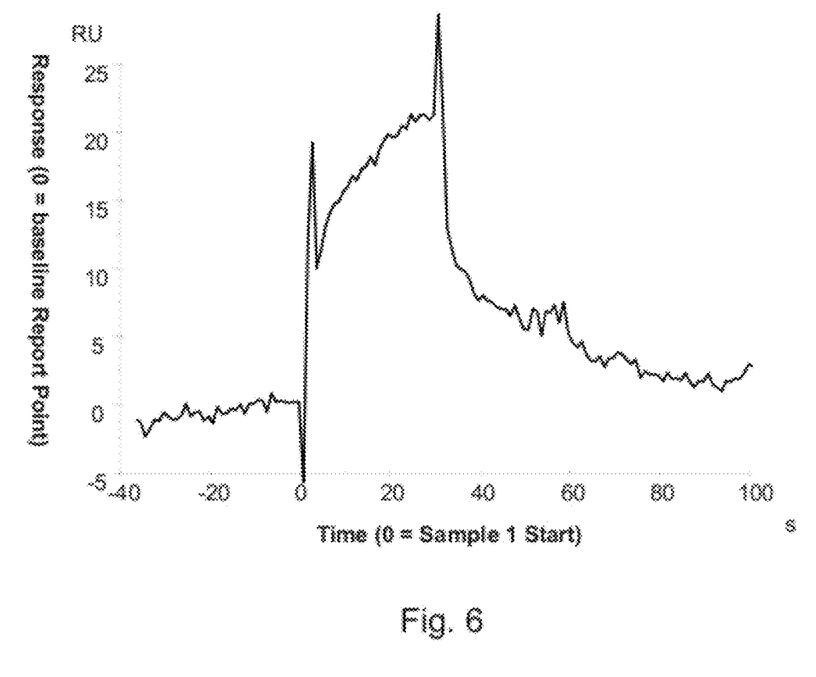
FIG. 6 shows an example of a response curve that display an increasing response during the injection.

According to one embodiment one binding behavior criteria is that the registered response increases at a rate exceeding a predetermined rate during analyte contact time. FIG. 6 shows an example of a response curve that display an increasing response during the injection, and one example of a criteria for the predetermined rate that may be used is for example >0.2 RU/s. Such a behavior might indicate secondary interactions that take place in addition to the interaction of study FIG. 4.

Figure 7:
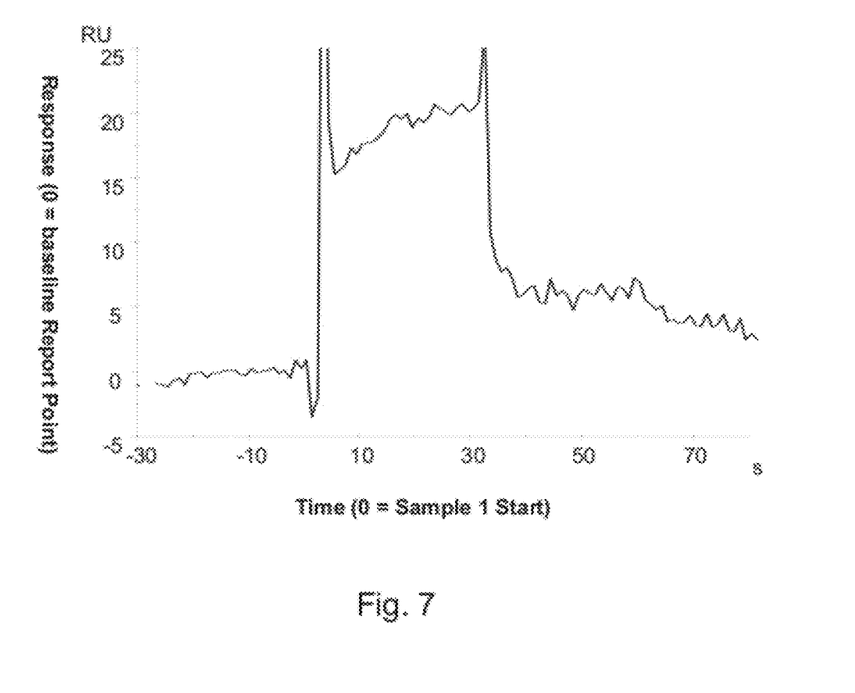
FIG. 7 shows an example of a response curve which has an elevated baseline after the injection.

According to one embodiment one binding behavior criteria is that the registered response exceeds a predetermined value after the analyte has been in contact with the sensor surface. FIG. 7 shows an example of a response curve that meets this type of criteria which has an elevated baseline after the injection. According to one embodiment, the predetermined value may be >3 RU. The presence of an elevated baseline after the injection may indicate a tight non-typical binding (for specific fragment) or aggregation.

According to one embodiment one binding behavior criteria is that the registered maximum response exceeds a predetermined value for the analyte interaction. This criteria is not directly related to the shape of the response curve but rather if the response exceeds the calculated or measured maximal response for the analyte interaction. According to one embodiment, the calculated or measured maximal response may be R>Rmax+5 RU, which indicates an alternative stoichiometry or additional aggregative interactions.

Investigators frequently want to exclude samples with this type of binding behavior from being selected for further investigations, which focus the resources on the primary selection. Even if the marked samples are not excluded it is important that the binding behavior information is attached to the collected data about the compound. Binding behavior markers are expected to be very useful tools when frequently evaluating large data sets improving the evaluation throughput significantly and thereby the overall screening throughput.

In the evaluation software disclosed herein these three parameters are indicated with point colors in the result plot along with a separate color for two or three of the different indications in combination, FIG. 5.

In this software solution the sensorgrams can be viewed by right clicking on the dots and information about the indications combined in the red dots is shown in the tool tip. The information is carried along to the result table and data export functionality.

According to one embodiment there is provided an analytical system for detecting molecular binding interactions, comprising:
(i) a biosensor comprising at least one sensing surface, detection means for detecting molecular binding interactions at the at least one sensing surface, and means for producing detection data representing binding curves, wherein each curve represents the progress of a binding interaction with time, and
(ii) data processing means for performing steps A to H of the above method.

The invention also extends to computer programs, particularly computer programs on or in a carrier, adapted for putting the method of the invention into practice. The carrier may be any entity or device capable of carrying the program. For example, the carrier may comprise a storage medium, such as a ROM, a CD ROM, a DVD or a semiconductor ROM, or a magnetic recording medium, for example a floppy disc or a hard disk. The carrier may also be a transmissible carrier, such as an electrical or optical signal which may be conveyed via electrical or optical cable or by radio or other means. Alternatively, the carrier may be an integrated circuit in which the program is embedded. Any medium known or developed that can store information suitable for use with a computer system may be used.

It is to be understood that the invention is not limited to the particular embodiments of the invention described above, but the scope of the invention will be established by the appended claims.

The invention claimed is:

1. A method of evaluating sensor response curves using a biosensor, the method comprising:
A: providing a sensor surface having a ligand immobilized thereto;
B: contacting the sensor surface with a plurality of analytes;
C: registering, using a processor, a plurality of sensor response curves, wherein each one of the plurality of sensor response curves corresponds to one of the plurality of analytes;
D: extracting, using the processor, interaction parameters from each sensor response curve;
E: applying, using the processor, one or more binding behavior criteria to evaluate the interaction parameters from each sensor response curve to determine a first subset of the interaction parameters meeting a binding behavior criterion and a second subset of the interaction parameters meeting another or no binding behavior criteria, wherein the one or more binding behavior criteria is:
a registered response increased at a rate of 0.2 RU/s or greater during analyte injection; or
an elevated baseline of 3 RU or greater relative to a pre-injection baseline after analyte injection has ceased; or
a measured response exceeding a calculated or measured maximal response for an analyte interaction by 5 RU or more; or any combination thereof;
F: determining a graphical representation for each interaction parameter based on at least one of the first subset or the second subset;
G: displaying, for selection via a computer display, the graphical representations of the interaction parameters as a plurality of points in a diagram, each of the plurality of points displayed in a first display configuration, each of the plurality of points selectable via the computer display, wherein each point is linked to its associated response curve, wherein the computer display facilitates user interaction to mark a point in the diagram to access the associated response curve in a second display configuration
H: facilitating selecting or deselecting of points, directly in the diagram via the computer display, based on the graphically distinguishable display of the points in the diagram, for processing of the plurality of response curves based on the one or more binding behavior criteria that are met, and I: excluding, using the processor, one or more response curves meeting the binding behavior criterion from selection for processing and reporting, wherein the biosensor is a surface plasmon resonance biosensor.

2. The method of claim 1, wherein interaction parameters relating to response curves meeting two or more binding behavior criteria are graphically distinguishable from interaction parameters relating to response curves meeting no or one binding behavior criteria.

3. The method of claim 1, wherein the sensor surface is regenerated between each analyte.

4. The method of claim 1, wherein the further processing of step G further comprises excluding points linked to response curves meeting the one or more binding behavior criteria in the further processing of the plurality of response curves.

5. The method of claim 1, wherein the further processing of step G further comprises attaching information of the one or more binding behavior criteria to the selected or deselected points.

6. The method of claim 1, wherein the further processing of step G further comprises automatically selecting and exporting the response curves exhibiting the one or more binding behavior criteria via a carrier to a computer device.

7. The method of claim 1, wherein the plurality of sensor response curves includes at least one hundred sensor response curves.

* * * * *